United States Patent [19]

Hu et al.

[11] Patent Number: 4,939,007
[45] Date of Patent: Jul. 3, 1990

[54] ARTICLE HAVING A HEMOCOMPATIBLE SURFACE

[75] Inventors: Can B. Hu; Donald D. Solomon, both of Spring Valley; Stanley C. Wells, Centerville, all of Ohio

[73] Assignee: Becton, Dickinson and Company, Franklin Lakes, N.J.

[21] Appl. No.: 164,948

[22] Filed: Mar. 7, 1988

[51] Int. Cl.⁵ .............................................. B29D 22/00
[52] U.S. Cl. .................................. 428/34.1; 428/364; 428/423.3; 428/423.7; 428/424.2; 428/425.5; 528/28; 523/112
[58] Field of Search ............... 428/423.3, 423.7, 424.2, 428/425.5, 364; 528/28; 523/112; 424/28

[56] References Cited

U.S. PATENT DOCUMENTS

| | | | |
|---|---|---|---|
| 3,562,352 | 2/1971 | Nyilas | 528/28 |
| 4,260,725 | 4/1981 | Keogh et al. | 525/419 |
| 4,423,099 | 12/1983 | Mueller et al. | 525/905 |
| 4,486,577 | 12/1984 | Mueller et al. | 525/479 |
| 4,521,564 | 6/1985 | Solomon et al. | 523/112 |
| 4,575,539 | 3/1986 | De Crosta et al. | 525/283 |
| 4,605,712 | 8/1986 | Mueller et al. | 525/474 |
| 4,613,517 | 9/1986 | Williams et al. | 424/78 |
| 4,647,643 | 3/1987 | Zdrahala et al. | 528/28 |
| 4,675,361 | 6/1987 | Ward | 525/92 |
| 4,764,560 | 8/1988 | Mitchell | 525/104 |
| 4,861,830 | 8/1989 | Ward | 525/92 |

FOREIGN PATENT DOCUMENTS 2140437 11/1984 United Kingdom .

*Primary Examiner*—Edith Buffalow
*Attorney, Agent, or Firm*—Richard E. Brown

[57] ABSTRACT

An article has a blood-contacting hemocompatible surface layer of a urethane-siloxane copolymer on a thermoplastic polymeric base material. The copolymer has siloxane segments prepared from hydroxyalkyl terminated polysiloxane glycols. The article is prepared by coextrusion of the base material and the copolymer.

9 Claims, 5 Drawing Sheets

ARTICLE HAVING A HEMOCOMPATIBLE SURFACE

FIELD OF THE INVENTION

This invention relates to biomedical devices, and more specifically relates to an article having a nonthrombogenic face and a method for its preparation.

BACKGROUND OF THE INVENTION

Extensive investigations have been undertaken over many years to find materials that will be biologically and chemically stable toward body fluids. This area of research has become increasingly important with the development of various objects and articles which can be in contact with blood, such as artificial organs, vascular grafts, probes, cannulas, catheters and the like.

Synthetic plastics have come to the fore as preferred materials for such articles. However, these materials have the major drawback of being thrombogenic. Thrombogenicity has conventionally been counteracted by the use of anticoagulants such as heparin. Exemplary of procedures for attachment of heparin to otherwise thrombogenic polymeric surfaces are the disclosures in U.S. Pat. No. 4,613,517 to Williams et al. and U.S. Pat. No. 4,521,564 to Solomon et al.

In general, the most blood compatible plastics known are the fluorinated polyolefins, such as polytetrafluoroethylene, and the silicone polymers. However, while being basically hemocompatible, silicone polymers do not have the desired mechanical strength for most blood-contacting applications. One approach to improving the mechanical properties of silicone polymers has been addition of appropriate fillers and curing agents. Such additives, although providing strength, are usually themselves thrombogenic so that the improved physical strength is offset by the reduced blood compatibility.

Another approach has been to combine the blood compatibility of the silicone with the excellent mechanical properties of polyurethane. U.S. Pat. No. 3,562,352 discloses a copolymer consisting of about 90% polyurethane and 10% polydimethylsiloxane. This material, under the trade name Cardiothane ® (Kontron Cardiovascular, Inc., Everett, MA), has been widely used in blood contacting applications, but has the major drawback that it is not thermoplastic and cannot be melt processed.

Thermoplastic polyoxyalkylene polyurethanes having up to 15% of a soft segment formed from a polysiloxane devoid of oxygen atoms bonded to both silicon and carbon are disclosed by Zdrahala et al. in U.S. Pat. No. 4,647,643. Polyurethanes prepared from 1,3-bis(4-hydroxybutyl) tetramethyl disiloxane are reported by Yilgor et al. in American Chemical Society Polymer Preprint 20, 286 (1982) and are suggested to have possible utility in the biomedical field.

Silicone coatings have been achieved by plasma polymerization of silicon-containing monomers onto various polymeric base materials. Preparation and hemocompatibility studies of such materials are described by Chawla in Biomaterials 2, 83 (1981).

Ward, in U.K. Patent GB No. 2,140,437B, disperses up to 5% of a silicone containing additive in a polymeric base material by mixing the components as a melt or in a solvent. Biomedical devices are prepared therefrom by conventional techniques such as injection molding and by homogeneous extrusion.

Flynn, in U.S. Pat. No. 4,581,390 discloses multiwall catheters prepared by coextrusion of a polymeric material and a composition containing a polyurethane having dispersed therein a platinum-cured silicone network polymer and a radiopaque material.

Multilayer films prepared by coextrusion are disclosed by DeAntonis et al. in U.S. Pat. No. 4,677,017.

While significant advances have been made toward blood compatible surfaces for fabrication of medical devices, further improvements are needed. In particular, materials having surfaces that are essentially nonthrombogenic for use in devices which will be in contact with blood for prolonged periods are needed. It is toward fulfillment of this need that this invention is directed.

SUMMARY OF THE INVENTION

One aspect of the present invention is an article having a hemocompatible surface. In the present disclosure, the term hemocompatible describes a surface that does not induce thrombosis or changes in blood cells, enzymes or electrolytes, does not damage adjacent tissue, and does not cause adverse immune responses or toxic reactions. Preferred articles are medical devices, such as catheters.

The article of the present invention includes a thermoplastic polymeric base material having thereon a layer of copolymer having urethane and silicon-containing segments. In preferred articles, the base material is a polyurethane and the silicon-containing segment is a siloxane. Particularly preferred articles have siloxane segments in the copolymer which are hydroxyalkyl terminated and which thereby have outstanding stability when in hydrolytic environments.

Another aspect of the invention is a method to prepare the article of the invention. The polymeric base material and the copolymer are codispensed, preferably coextruded, whereby a layer of the copolymer is formed on the base material.

Thus, the invention provides an article having a hemocompatible surface which is substantially nonthrombogenic and which is highly stable toward hydrolysis when in contact with blood. The blood contacting surface is a polyurethane in which the glycol component is exclusively or predominantly a siloxane. Further, the blood contacting siloxane of the preferred composition is exclusively or substantially an hydroxyalkyl terminated siloxane thereby precluding hydrolysis of the siloxane by the blood or other body fluid. The composition of the invention preferably is prepared by coextrusion. In contrast, the conventional process of plasma depositing a polysiloxane on a polyurethane is inapplicable to the preparation of an article having a copolymeric layer of oxyalkyl-terminated siloxane-containing polyurethane on a polymeric base material.

DETAILED DESCRIPTION OF THE INVENTION

While this invention is satisfied by embodiments in many different forms, there will herein be described in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, an article is prepared by codispensing two or more thermoplastic polymeric materials so that one of the polymeric materials is layered on another of the materials. At least one of the polymeric materials forming the article is hemocompatible whereby any surface desired of the article and therefore any surface of a biomedical device fabricated in accordance with the method of the invention nonthrombogenic. Nonlimiting examples of biomedical devices contemplated to be fabricated by the method of the invention are catheters, tubing, artificial hearts, valves, membranes, grafts and the like.

Fabrication is generally defined as the physical, mechanical or thermal manipulation of a polymer into a form such as, for example, a tubing, fiber, sheet or film, or a device suitable for a specific application. In accordance with the present invention, comolding or, preferably, coextruding processes are used for fabrication. In the preferred method of the invention, a base material, preferably a polyurethane, and a urethane-siloxane copolymer are coextruded using a conventional apparatus 10, schematically illustrated in FIG. 1, to give a multiwall tubing.

Figure 1:
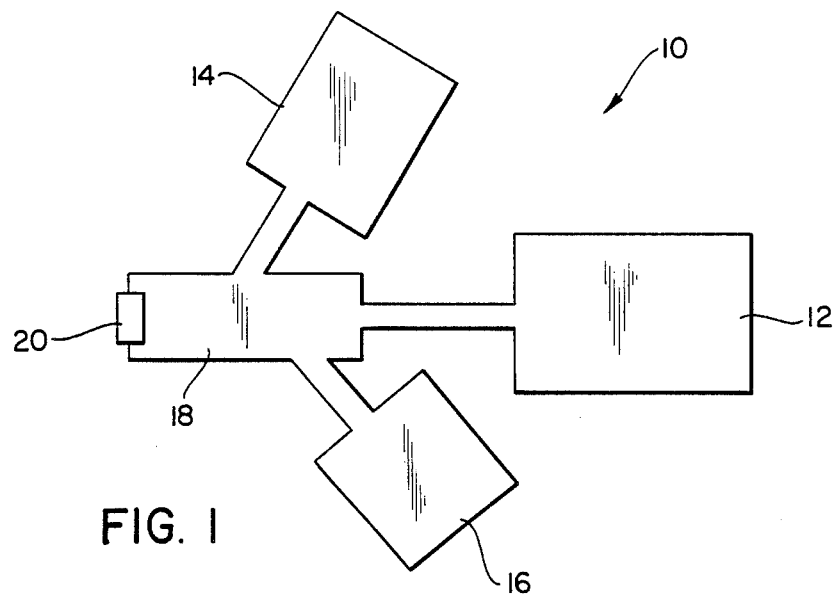
FIG. 1 is a block diagram of a coextrusion apparatus useful in the invention.

In FIG. 1, polymer melt streams from at least two of a main extruder 12 and two coextruders 14 and 16 are maintained separately until combined as continuous concentric rings in the forward, i.e., downstream portion of an extruder head 18, from which they subsequently pass through and emerge from a tube die 20 as an integral tubing member. Die 20 itself, as known in the art, may be coaxial or crosshead, or, if desired for the application intended, multiple dies including both types, may be used.

When using such an apparatus, it is seen that conventional extrusion using only the main extruder 12 may give a single component tubing, or one or more of coextruders 14 and 16 may be used to give the desired number of layers in the tubing. Suitable coextrusion apparatus may be purchased for example, from Genca Cable Company, Clearwater, FL or from Wayne Machine and Die Company, Totowa, NJ, or if desired, custom coextrusion apparatus can be designed for fabrication of any specific article of the invention.

Figure 2:
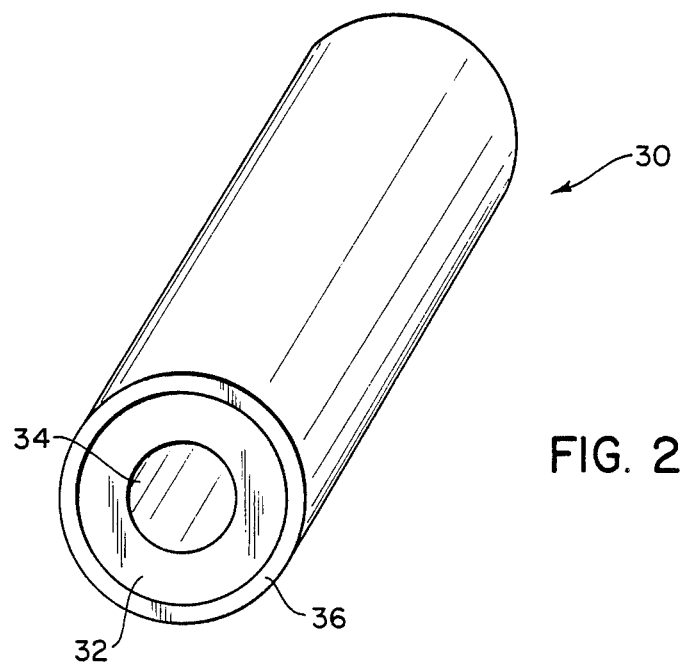
FIGS. 2–4 are perspective views of representative coextruded tubings of the invention.
Figure 3:
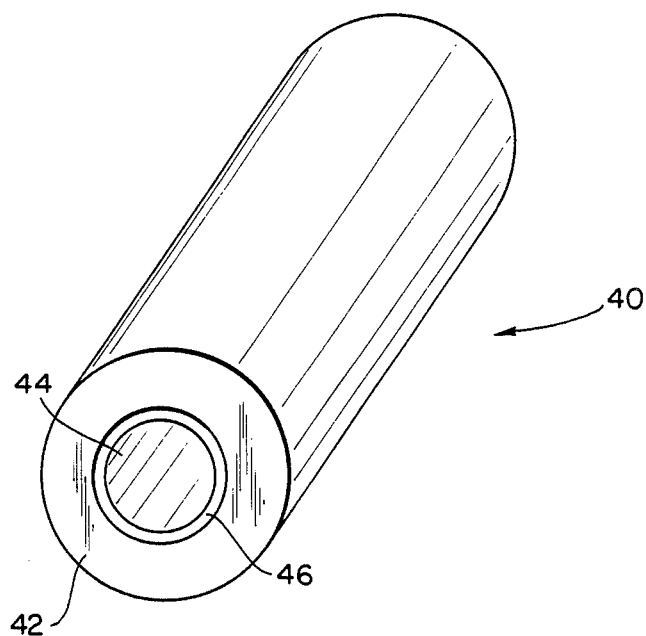
Figure 4:
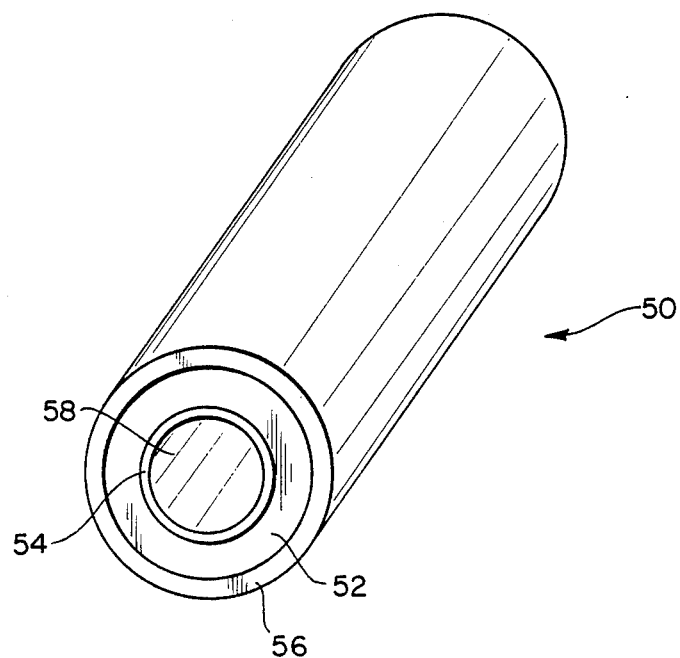

When a polyurethane and a urethane-siloxane copolymer are coextruded from main extruder 12 and coextruder 14 or 16, a tubing of the invention having a layer of copolymer on the polyurethane is obtained. FIG. 2 illustrates a typical two-layer tubing of the invention wherein tubing 30 has polyurethane layer 32 defining lumen 34 and copolymer 36 layered on the polyurethane. If it is desired to place the copolymer on the lumen wall of the polyurethane tubing, main extruder 12 may be used for the copolymer and one of the coextruders used for the polyurethane. FIG. 3 illustrates a two-layer tubing 40 having copolymer layer 46 defining lumen 44 and polyurethane layer 42 layered on the copolymer. Further, a polyurethane tubing having urethanesiloxane layers on both the outside surface of the polyurethane and on the lumen wall may be obtained merely by triextrusion of the melts from the appropriate extruders. (In the present disclosure, simultaneous extrusion of three layers is termed triextrusion.) It is evident that the layers on the outside surface and the lumen wall may be of the same or different compositions.

In another embodiment of the tubing of the invention, triextrusion of the polyurethane, urethane-siloxane copolymer and a tie-layer provides a tubing having the polyurethane and copolymer layers securely bonded by an intervening tie-layer. Tie-layers are conventional in the art and are described by DeAntonis et al., supra. A particularly suitable apparatus for triextrusion is the tri-layer die for medical tubing available from Genca Cable Co.

By proper selection of extruders, coextruders and dies, the thickness of the layers and thereby the weight percentages of the base polymer and the copolymer may be adjusted according to the requirements of the particular coextruded article. Preferred articles of the invention, contain from 50 to 99% by weight of the base polymer and from 1 to 50% by weight of the copolymer. The most preferred article is a polyurethane tubing of 0.4 to 6.0 mm diameter with a layer of urethane-siloxane copolymer of 0.01 to 0.2 mm thickness thereon.

The base polymer provides the article with desirable mechanical properties such as tensile strength thermoplasticity and flexibility. While the invention contemplates use of any polymeric or copolymeric base material which provides these attributes, preferred base materials are polyolefins, such as polyethylene and polypropylene, polyesters, polyurethaneureas and, most preferably, polyurethanes.

Polyurethanes suitable as base materials may be prepared from a diisocyanate, a polyglycol and optionally a chain extender. Suitable diisocyanates are aromatic diisocyanates such as diphenylmethane-4,4'-diisocyanate, (MDI), diphenylmethane-3,3'-diisocyanate, alicyclic diisocyanates such as isophorone diisocyanate and dicyclohexylmethane-4,4'-diisocyanate, and aliphatic diisocyanates, as, for example, hexamethylene diisocyanate. The most preferred diisocyanate is MDI.

The polyglycol may be either a polyether glycol, a polyester glycol or mixtures thereof. Suitable polyether glycols are, for example, polyethylene oxide, polypropylene oxide or polytetramethylene oxide or mixtures thereof. The preferred polyglycol is polytetramethylene oxide having a molecular weight of from about 600 to 3300 or mixtures thereof. The most preferred polyglycols are polytetramethylene oxides having average molecular weights of 1000 and 2000.

Polyester glycols which may be used to prepare the polyurethane component of the composition may be obtained by esterifying a dicarboxylic acid with a glycol. Preferred polyester glycols are, for example, polycaprolactone, polyethylene adipate, polybutylene adipate and polyhexamethylene adipate.

The optional chain extender may be a low molecular weight branched or unbranched diol of up to 10 carbon atoms, or mixtures thereof. Representative nonlimiting examples of chain extenders are ethylene glycol; diethylene glycol; triethylene glycol; 1,2-propanediol; 1,3-propanediol; 1,6-hexanediol; 1,4-bis-hydroxymethyl cyclohexane, hydroquinone dihydroxyethyl ether, and, preferably butanediol (BD).

Suitable polyurethane base materials have a Shore hardness range of from about 40A to 75D and a tensile strength of about 3,000–10,000 psi. Calculation of component ratios to give polyurethanes within the above Shore hardness range is easily within the purview of one skilled in the art. Likewise, procedures for polyurethane synthesis from the above components are conventional, and no details in this respect are needed for a complete understanding of the invention by one skilled in the art.

In accordance with the method of the invention, a layer of urethane-siloxane copolymer having a Shore hardness of about 45A to 60D is coextruded onto a surface of the polyurethane base material. The copolymer may be prepared from any isocyanate and chain extender as described above for the polyurethane base material. The polyglycol component of the copolymer may be a conventional polysiloxane glycol of general structure I or it may be a modified polysiloxane glycol of general structures II, III and IV:

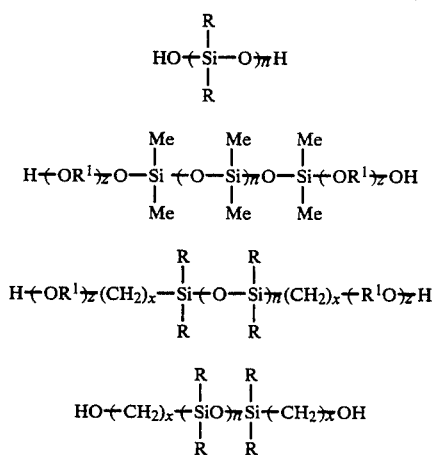

In structures I–IV, R may be a lower alkyl group, branched or unbranched, of about 1–6, preferably 1–3, carbon atoms; $R^1$ may be a lower alkylene group, branched or unbranched, of about 1–6, preferably 1–3, carbon atoms; z has an average value of 1 to 45; X may be an integer of about 2–10, preferably 2–6, most preferably 3–4; n may be an integer such that the molecular weight of the polyglycol may be from about 600–60,000, preferably from about 1,000–5,000 and most preferably about 2,000.

Glycols of structure II have been described by Rauner et al. (U.S. Pat. No. 4,057,595). Glycols of structure III have been described by Zdrahala et al., supra.

It is preferred to prepare the copolymer from a polyglycol of structure IV. Such polyglycols are conventionally referred to as hydroxyalkyl terminated silicone fluids. They may be purchased from, for example, Silar Laboratories, Scotia, N.Y. The most preferred polyglycol for preparation of the copolymer of the invention is hydroxybutyl terminated polydimethylsiloxane of molecular weight about 2000.

The copolymer prepared from a glycol of structure IV has hydroxyalkyl terminated polysiloxane segments linked to urethane segments derived from the isocyanate. Preferred copolymers have a tensile strength of about 1000–5000 psi. Calculation of component ratios to give a urethane-siloxane copolymer within the above Shore hardness range is conventional and well known to those skilled in the art.

Preparation of the urethane-siloxane copolymer of the invention from the above-described isocyanate, chain extender and polysiloxane glycol may be carried out by any conventional technique for polyurethane synthesis, and no further details with respect to copolymer synthesis are needed for a complete understanding of the invention. A feature of the invention is that the copolymer which forms the blood contacting surface of the article may be prepared from the components without adding a polymerization catalyst. Conventional catalysts in the art, for example, organometallic compounds such as dibutyl tin dilaurate and stannous octoate, are leachable and may cause deleterious effects on the hemocompatibility of the final product.

The surface of the article of the invention having a layer of urethane-siloxane copolymer on a polyurethane base material may be analyzed by conventional election spectroscopy for chemical analysis (ESCA). The results of this analysis are given in Example III.

The surface of the article may be tested for hemocompatibility by in vivo scintigraphy. In this procedure, as described by Solomon et al. in Journal of Biomedical Materials Research, 21 43 (1987), platelet adhesion as a function of time and thrombus weight for the tubing of the invention are compared to a control thermoplastic aromatic polyetherpolyurethane tubing having a Shore hardness of 50D, a number average molecular weight of 35,000 and a weight average molecular weight of 100,000 (hereinafter referred to as the control polyurethane tubing). This study shows a 35% decrease in platelet adhesion and a 60% decrease in thrombus weight.

EXAMPLE I

General Procedure for Copolymer Synthesis

Hydroxybutyl terminated silicone fluid of about 2000 MW (60 g, Silar Labs, Scotia, NY) and 100 ml of mixed solvent (50 ml each of dimethylacetamide and 2-ethoxyethyl ether) were charged to a resin kettle. A solution of 25 g MDI in 100 ml of the above mixed solvent was added with stirring, and the mixture stirred one additional hour at 60–70° C. After cooling to 30° C., 6.3 g of BD in 100 ml of mixed solvent were added. Stirring was continued for one hour, and the mixture was heated at 45° C. for one hour. The polymer was recovered by evaporating the solvent at 70° C. and was ready for coextrusion by the method of Example II.

EXAMPLE II

A thermoplastic aromatic polyetherpolyurethane having a Shore hardness of 40D, a number average molecular weight of 13,500, a weight average molecular weight of 39,000, a glass transition temperature of −50° C. and a melting temperature of 149° C. was coextruded with a layer of the silicone urethane copolymer from Example I having a glass transition temperature of −118° C. and a melting temperature of 174° C. The polyurethane was extruded through a ¾ inch diameter extruder having a temperature profile of zone 1, 138° C., zone 2, 182° C. and zone 3, 191° C. at a screw speed of 20 rpm, a barrel pressure of 1100 psig, and a motor drive load of 1.2 amps. The silicone-urethane copolymer was extruded through a ½ inch diameter extruder having a temperature profile of zone 1, 149° C., zone 2, 188° C., and zone 3, 193° C. at a screw speed of 15 rpm, a barrel pressure of 800 psig and a motor drive load of 0.4 amps. The extrudates were passed through a Genca coextrusion die at about 193° C. A catheter tubing was thus obtained having an outside diameter of 66 mils, an inside diameter of 45 mils and wall thickness of 10-11 mils. The thickness of the silicone-urethane copolymer layer was about 1-2 mils. The multilayer catheter had a uniform appearance.

EXAMPLE III

The surface of the control polyurethane tubing, the coextruded sample of Example II and pure silicone-urethane copolymer were examined by ESCA using an AEI-100 photoelectron spectrometer modified to include a 20 liter/sec turbomolecular pump and a 110 liter/sec ion pump to speed up the evacuation and minimize the contamination of the sample chamber. The window was set at 20 eV for all the elements to obtain a better resolution. A scanning rate of 2 eV/sec was used for all experiments.

Figure 5:
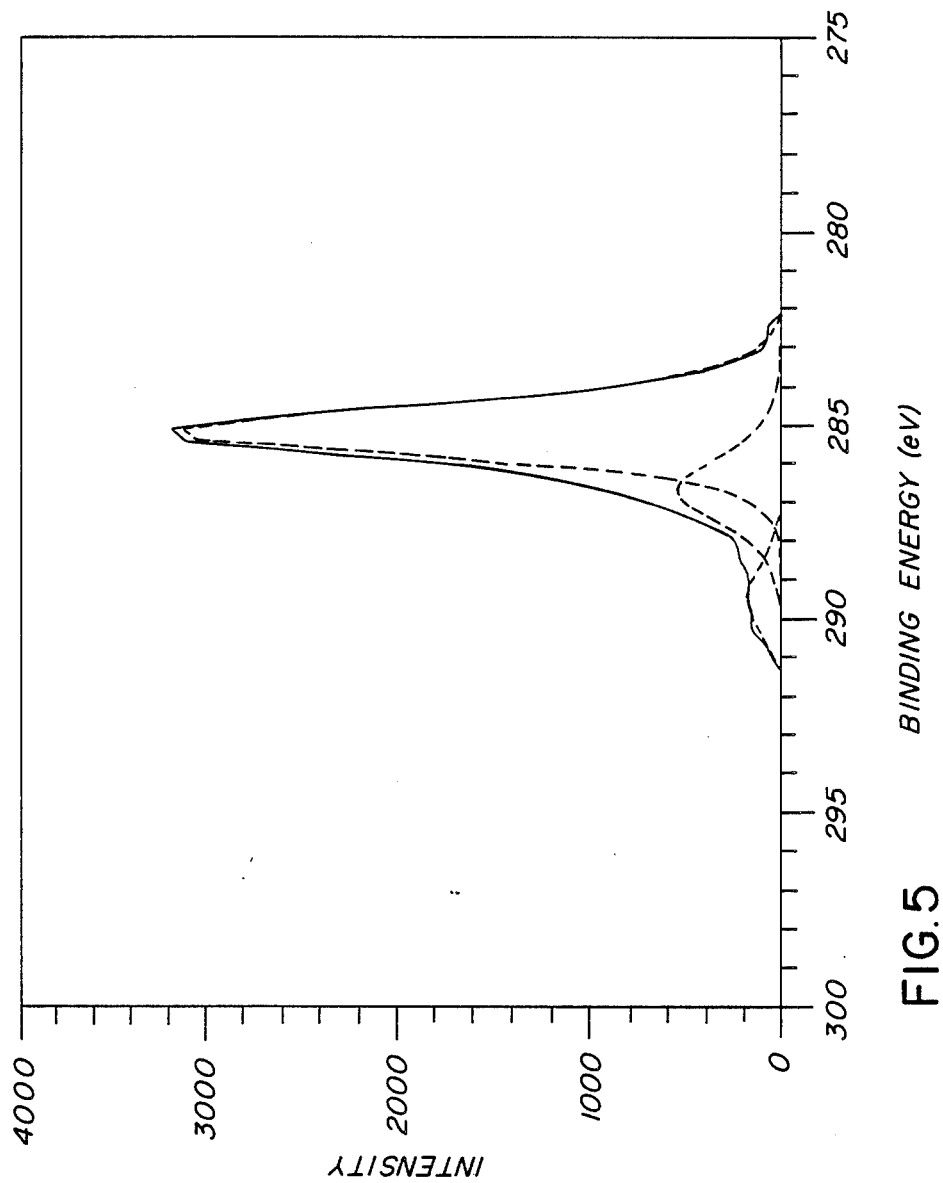
FIG. 5 is a plot of the surface chemistry of the composition of the invention.
Figure 6:
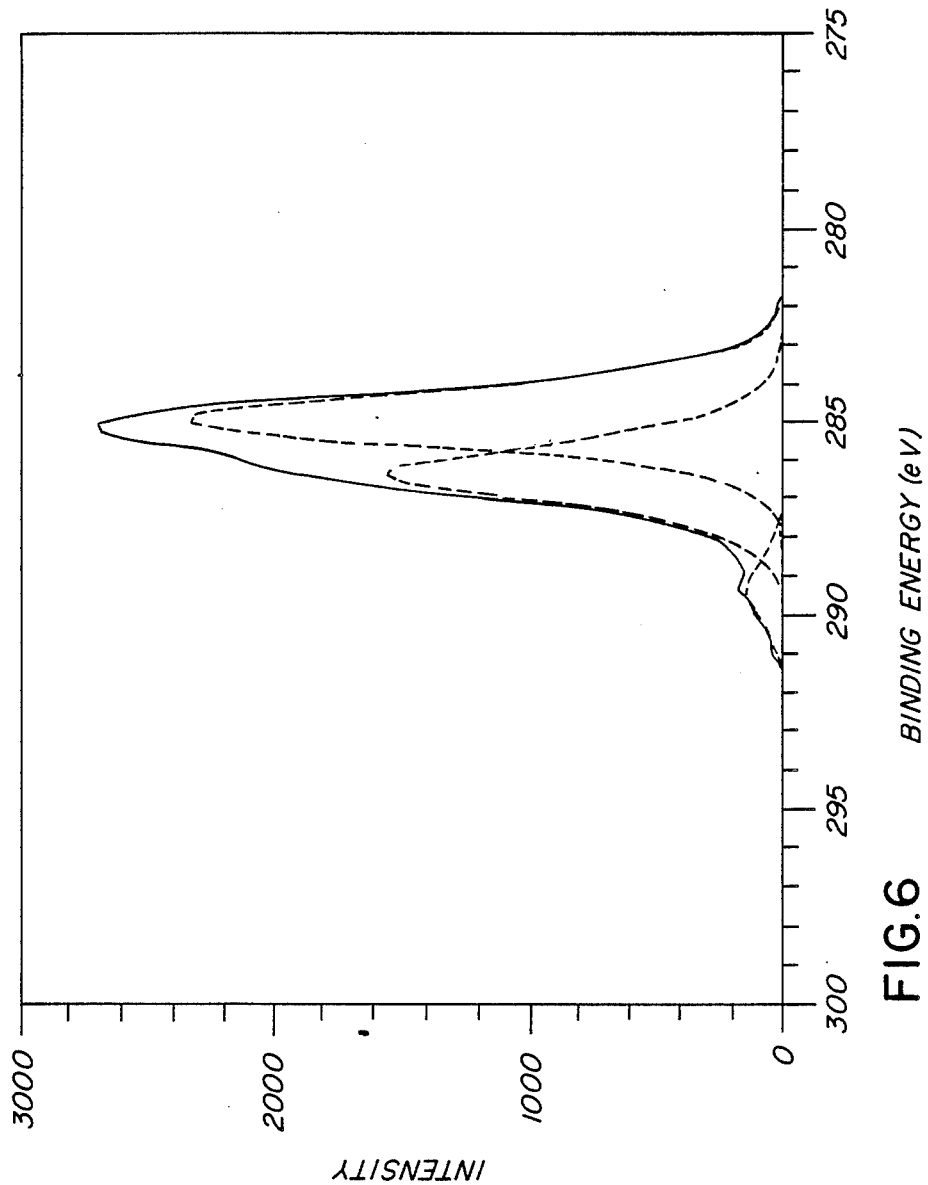
FIGS. 6 and 7 are plots of the surface chemistry of control base polymer and copolymer respectively.
Figure 7:
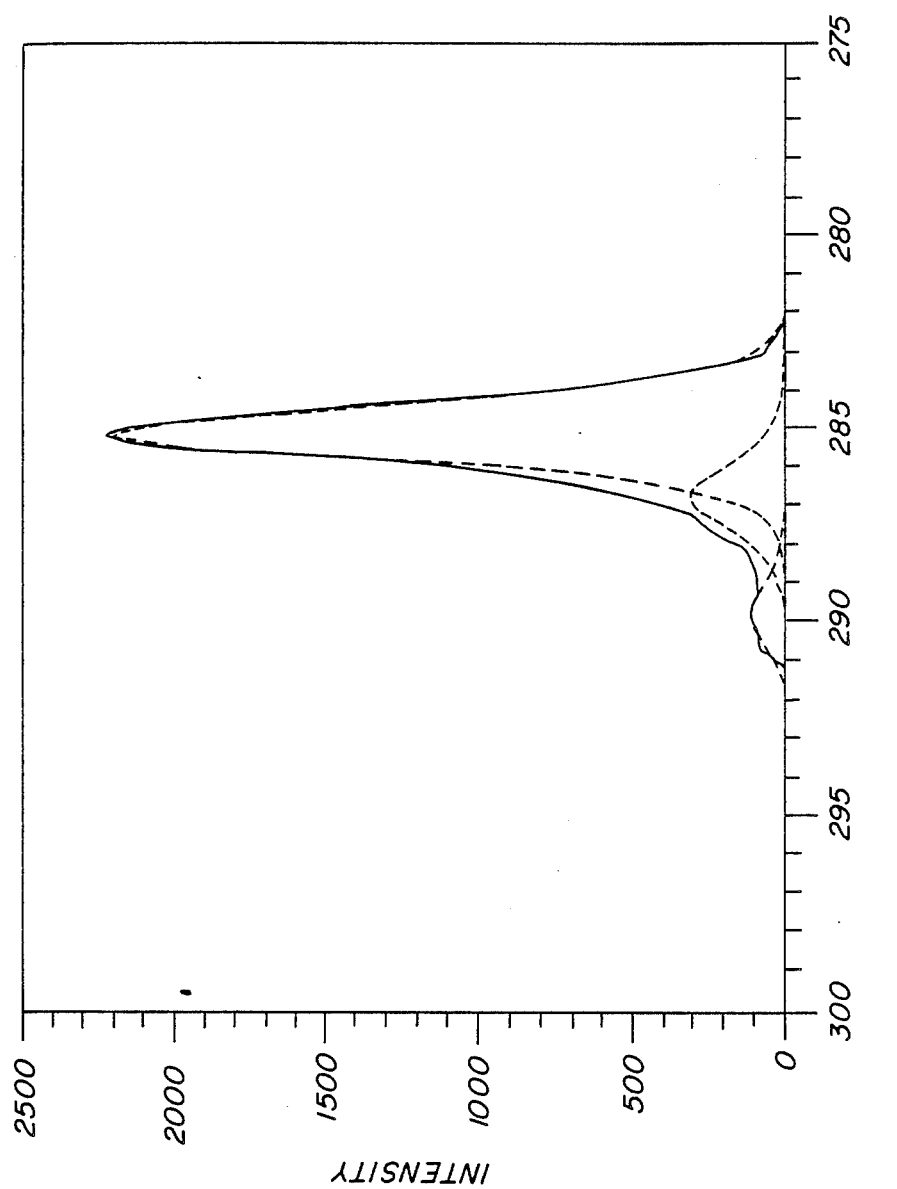

Scans of carbon atoms in the coextruded tubing of Example II, the control polyurethane tubing and pure copolymer of Example I are shown in FIGS. 5, 6 and 7 respectively. In the control tubing, two peaks of approximately equal size at 285 and 286.5 eV were observed. However, in the coextruded tubing and the pure silicone-urethane copolymer, one major peak at 285 eV and a much smaller peak at 286.5 eV were observed. The peak at 285 eV was due to carbon-carbon or carbon-silicon bonds, while the peak at 286.5 eV was due to carbon-oxygen bonds. The significant decrease of carbon-oxygen in the surface of the coextruded tubing indicated that a homogeneous silicone-urethane copolymer had formed on the external surface of the base polymer. In addition, the scans of the coextruded tubing and the pure copolymer were essentially superimposable, also indicating complete and homogeneous coverage of the base polymer with the copolymer.

From the scans, the percentage elemental compositions were determined and are summarized as given the chart below.

|  | Si | C | | | COO | N | O |
|---|---|---|---|---|---|---|---|
|  |  | C—C C—Si | C—O | | | | |
| Silicone-urethane Copolymer of Example I | 13.1 | 46.4 | 10.5 | | 3.1 | 3.3 | 23.7 |
| Coextruded Tubing of Example II | 14.6 | 48.9 | 8.1 | | 2.4 | 2.0 | 24.2 |
| Control Polyurethane Tubing | 3.0 | 40.3 | 31.0 | | 2.7 | 2.0 | 21.1 |

It is clear from the table that the surface chemical composition of the coextruded tubing of the invention is almost the same as that of the silicone-urethane copolymer, indicating that a complete and uniform silicone-urethane layer was obtained by this coextrusion process.

EXAMPLE IV

In Vivo Hemocompatibility Study

The control polyurethane tubing was inserted into one jugular vein of a dog and the coextruded tubing of Example II was inserted into the other jugular vein of the same animal (in order to neutralize dog to dog variation). Platelet adhesion and thrombus deposition were determined by the procedures of Solomon et al. (supra) from the average platelet uptake slope and thrombus weight from three dogs.

|  | Coextruded Tubing | Control polyurethane tubing |
|---|---|---|
| Slope | 0.092 ± 0.008 | 0.140 ± 0.022 |
| Thrombus Weight | 18.0 ± 10.4 mg | 43.9 ± 18.7 mg |

It is clear that the coextrusion process of the invention provides a coextruded tubing having lower platelet adhesion and lower thrombus weight.

What is claimed is:

1. An article having a hemocompatible surface comprising a thermoplastic polymeric base material having thereon a layer of a copolymer comprising a polyurethane segment and a hydroxyalkyl-terminated siloxane segment said layer being from 5 to 50% by weight of said material.

2. The article of claim 1 wherein said base material is selected from the group consisting of polyurethane, polyolefin, polyester and polyurethaneurea.

3. The article of claim 2 wherein said polyurethane has a Shore hardness of about 50A to 75D.

4. The article of claim 1 which is in the form of a tubing.

5. The article of claim 1 which is in the form of a fiber.

6. The article of claim 1 which is in the form of a sheet.

7. The article of claim 1 which is in the form of a film.

8. An article having a hemocompatible surface comprising a thermoplastic polyurethane base material of Shore hardness about 40A to 75D having thereon a layer of a copolymer comprising a polyurethane segment and a hydroxyalkyl- terminated polydimethyl siloxane segment said layer being from 5 to 50% by weight of said material.

9. The article of claim 8 which is a catheter.

* * * * *